Nov. 26, 1963 H. R. BRIXEY Plant Pat. 2,314

CHERRY TREE

Filed Aug. 19, 1960

Homer R. Brixey
INVENTOR.

BY Clarence A. O'Brien and Harvey B. Jacobson
Attorneys

United States Patent Office

Plant Pat. 2,314
Patented Nov. 26, 1963

2,314
CHERRY TREE

Homer R. Brixey, 2145 N. Evans, McMinnville, Oreg.

Filed Aug. 19, 1960, Ser. No. 50,815
1 Claim. (Cl. Plt.—37)

The present discovery relates to a new and distinct cherry tree. The new and patentable characteristic thereof resides in the dwarfing effect of the rootstock on domesticated fruiting cherry trees.

This new variety is a cross made by the applicant of two Oriental cherry trees native to China which were not clearly defined varieties but were most closely related to *Prunus serrulata.*

For various reasons the dwarfing of standard varieties of fruiting cherry trees is desirable; for example, the resulting facility in picking and harvesting the cherries, and the spraying and caring for the trees. Also, dwarfing is of advantage in planting fruiting cherry trees in a limited space.

The existing so-called "dwarf cherry trees" are only a little less vigorous than a tree on its normal root. Generally, the dwarfing is simply a slower action in obtaining a given size. Actually, dwarf cherry trees in standard varieties now being sold are misnomers, since the dwarfing effect is nothing more than a slight retardation of normal growth.

The desirability of my new cherry tree relates primarily to the effect it has on standard fruiting cherry trees as an understock, a standard or trunk, or as a double working graft, when grafted under the desired variety to be dwarfed. The standard variety then exhibits sturdy, stocky, mature growth and starts to bear fruit rather than making youthful, vigorous, elongated, unproductive growth.

My new variety has been asexually reproduced at my nursery in McMinnville, Oregon, by stooling, by a double working graft inserted in the trunk or standard of known varieties of cherry trees, and by rooting cuttings.

Figure 1:
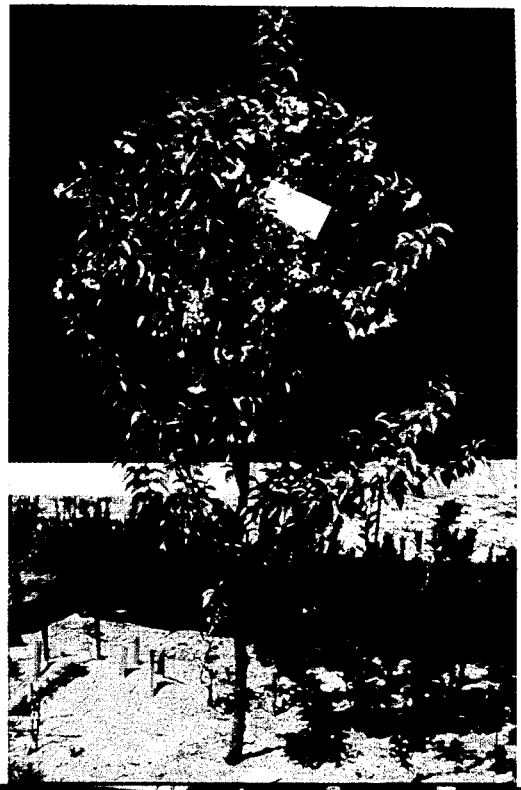
Figure 2:
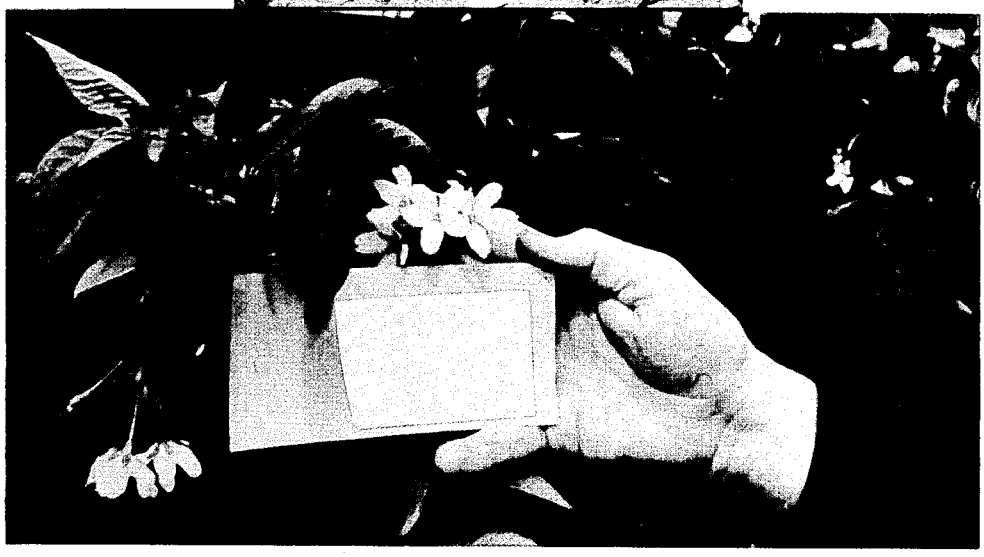

The drawings show in FIG. 1 a five-year old tree and in FIG. 2 the foliage and bloom thereof.

The cherry tree, were it to be grown itself, has the following characteristics:

Leaves: Ovate acuminate, very pointed oval shaped, very serrate. Serrations approximately 1/10 inch in length, with 10 to 14 to the inch, doubly serrate. Similar to Mazzard in size, approximately 6 inches long.

Growth: More spreading and slower than Mazzard. Rootstock will stool and lends itself well to vegetative or asexual reproduction.

Compatibility: The subject variety has been found to be compatible with the following standard fruiting trees: Black Giant, Black Republican, Lambert, Van, Royal Ann and Bing; with Kentish, Montmorency, Royal Duke, and Late Duke (Sour); with Mazzard and Mahaleb (Rootstocks); and with Kwanzan and Shirofugen (Flowering).

Graftage: Compatible, no offset, stricture or bulging.

Hardiness: Hardy as Mazzard.

Disease free: No gummosis, although standard varieties died in some cases in check plot to test incidence of disease.

Nodes: Appressed, or about two nodes to one of Mazzard in a given area of stem.

Buds: Foliage buds narrow, elongated and pointed, set at 25–45 degrees to the stem.

Stems: Light colored, tan as compared with the dark brown of Mazzard. About ½ the diameter of Mazzard under similar conditions and area.

Blooms: About 10 days earlier than Mazzard; somewhat similar.

Fruit: Small, black, slightly elongated.

Parentage: A hybrid, the cross of two Oriental cherry trees collected on the Shantung Peninsula, near Tsingtao, Chino. The cherry trees exhibited some of the characteristics of *Prunus subhirtella, Prunus yedoendis,* but mostly were identified as *Prunus serrulata* by the late Dr. Albert N. Steward.

Having thus disclosed the invention, I claim:

A new and distinct cherry tree herein shown and described characterized as to novelty by its consistent dwarfing effect on domesticated fruiting cherry trees.

No references cited.